United States Patent [19]

Redey et al.

[11] 4,414,093

[45] Nov. 8, 1983

[54] MULTIFUNCTIONAL REFERENCE ELECTRODE

[75] Inventors: Laszlo Redey, Lisle; Donald R. Vissers, Naperville, both of Ill.

[73] Assignee: The United States of America as represented by the U.S. Department of Energy, Washington, D.C.

[21] Appl. No.: 335,997

[22] Filed: Dec. 30, 1981

[51] Int. Cl.³ ............................................ G01N 27/30
[52] U.S. Cl. .................................. 204/412; 204/408; 204/435
[58] Field of Search ........... 204/195 F, 195 M, 195 L, 204/195 S, 435, 408, 412; 128/635; 429/101, 102, 103, 104, 112

[56] References Cited

U.S. PATENT DOCUMENTS 3,864,232  2/1975  Handman et al. ................. 204/195 S

OTHER PUBLICATIONS

H. V. Venkatasetty, "Proc. Symposium on Lithium Batteries", pp. 392–401, (1981).

Robert K. Steunenberg, "Research & Development Program on Lithium/Iron Sulfide Batteries", (1981).
The Electrochem. Soc. Extended Abstracts, vol. 80-2, pp. 220–223, (1980).
Laszlo Redey et al., "Design & Development of Micro-Ref. Electrodes for the Lithium/Metal–Sulfide Cell System", (1979).
Fisher Electrode Handbook, pp. 4–5 & 27, (1981).
Omega Engineering Inc., Bulletin B-15, (1981).

*Primary Examiner*—G. L. Kaplan
*Attorney, Agent, or Firm*—Hugh W. Glenn; Robert J. Fisher; Richard G. Besha

[57] ABSTRACT

A multifunctional, low mass reference electrode of a nickel tube, thermocouple means inside the nickel tube electrically insulated therefrom for measuring the temperature thereof, a housing surrounding the nickel tube, an electrolyte having a fixed sulfide ion activity between the housing and the outer surface of the nickel tube forming the nickel/nickel sulfide/sulfide half-cell. An ion diffusion barrier is associated with the housing in contact with the electrolyte. Also disclosed is a cell using the reference electrode to measure characteristics of a working electrode.

15 Claims, 3 Drawing Figures

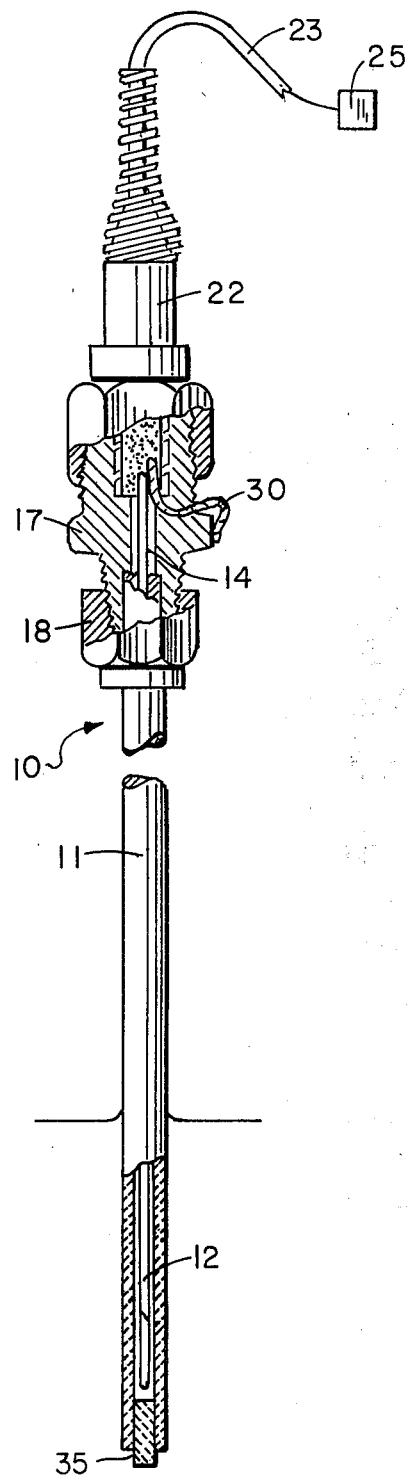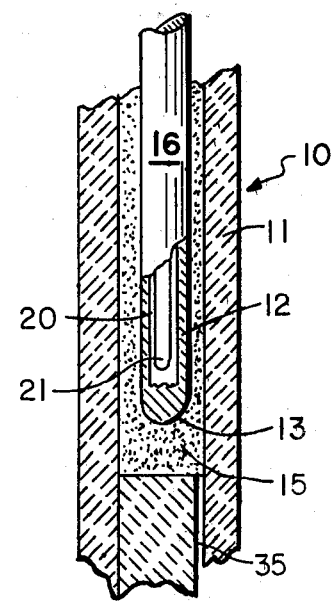
FIG. 1
FIG. 2

MULTIFUNCTIONAL REFERENCE ELECTRODE

CONTRACTUAL ORIGIN OF THE INVENTION

The invention described herein was made in the course of, or under, a contract with the UNITED STATES DEPARTMENT OF ENERGY.

BACKGROUND OF THE INVENTION

The present invention relates to a multifunctional reference electrode having both temperature and voltage sensing elements in the same device for use in an electrochemical cell. More particularly, the invention relates to a sensing device in which a hollow half-cell electrode serves as the housing for temperature sensing means to measure the temperature of the half-cell thereby permitting a precise correlation between temperature and voltage. The reference electrode has been designed for use in high temperature lithium-aluminum/metal sulfide cell systems but has other uses as hereinafter set forth.

In the development of a lithium-aluminum/metal sulfide cell, it is important that a known reference electrode potential be generated by an electrical double layer in the reference electrode with which to measure the potential difference between the reference electrode and the electrode of interest. At a cell operating temperature of about 400° C., temperature variations across the cell in the order of about 50° C. have been detected, thereby causing the voltage of the half cell with respect to the electrode of interest to vary considerably. The change in voltage, if undetected, prevents an effective determination of cell voltages under various conditions of cell operations. For example, temperature effects may cause the cell voltage to change by values in the order of at least 12 mV, while it is important to detect changes in the cell voltage on the order of 3-4 mV with an accuracy of about 1 mV. Since voltage of these cells is temperature dependent, it is essentially impossible to measure and calculate the potential of the electrode of interest without precise knowledge of the reference electrode temperature.

The multifunctional reference electrode of the present invention has been used in the development and design of the lithium-aluminum/metal sulfide battery. The reference electrode is also useful in the development of any battery as well as having other applications such as for pH electrodes, indicator electrodes, and the like in various fields of industrial processes, environmental control and research.

Heretofore, no device has been available which will precisely measure the temperature of the reference electrode in the area where the electrode potential is produced. The reference electrode of the present invention provides extremely accurate temperature measurements at the surface where the electrode potential is produced, thereby permitting accurate calculations for the electrode of interest.

SUMMARY OF THE INVENTION

It is an object of the present invention to provide a reference electrode with means for determining the temperature of the reference electrode under working conditions.

An important object of the present invention is to provide a multifunctional reference electrode, comprising a metal tube, a means inside the metal tube for measuring the temperature thereof, a housing surrounding the metal tube, an electrolyte having a fixed ion activity between the housing and the outer surface of the metal tube, and an ion diffusion barrier associated with the housing in contact with the electrolyte, whereby the multifunctional reference electrode provides a temperature dependent electron pressure at the surface of the metal tube when an electrochemical double-layer exists between the metal tube outer surface and the electrolyte in combination with means for measuring the temperature of the metal tube.

Still another object of the present invention is to provide an electrochemical cell comprising a working electrode and a reference electrode and a first electrolyte in communication with both electrodes, the reference electrode including a metal tube, means inside the metal tube electrically insulated therefrom for measuring the temperature thereof, a housing surrounding the metal tube, a second electrolyte having a fixed ion activity between the housing and the outer surface of the metal tube providing a temperature dependent electrode potential at the surface of the metal tube when an electrochemical double-layer exists between the metal tube outer surface and the second electrolyte, an ion diffusion barrier associated with the housing providing communication between ions of the first and second electrolytes, and means for measuring the potential difference between the reference electrode and the working electrode, whereby the fixed ion activity and measured temperature of the reference electrode and the potential difference between the reference electrode and the working electrode provides a value for the electrode potential at the working electrode.

These and other objects of the present invention may be more readily understood when taken in conjunction with the following specification and drawings, in which:

DESCRIPTION OF THE FIGURES

FIG. 1 is a side elevational view partly in section of the reference electrode of the present invention;

FIG. 2 is an enlarged view of the bottom portion of the reference electrode illustrated in FIG. 1.

DETAILED DESCRIPTION OF THE INVENTION

Figure 3:
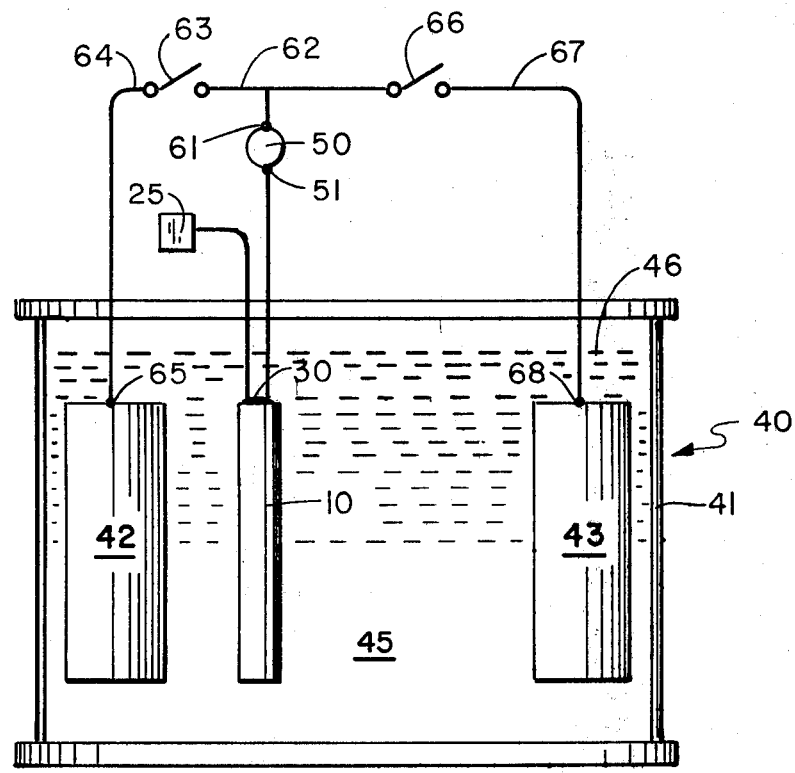
FIG. 3 is a schematic illustration of an electrochemical cell utilizing two working electrodes and the reference electrode of the subject invention.

Referring now to FIGS. 1 and 2 of the drawings, there is disclosed the reference electrode 10 of the subject invention including an elongated ceramic tubular housing 11 having positioned therewithin extending axially thereof an electrical connection means such as a smaller diameter metal tube 12 having a closed bottom 13 and a top 14. An electrolyte 15 is interposed between the ceramic tubular housing 11 and the outer surface 16 of the metal tube 12. The reference electrode 10 is provided with an electrode head 17 and a threaded connector 18 suitably interconnecting the housing 11 with the head 17.

A thermosensor 20 extends downwardly within the metal tube 12 and may be electrically insulated therefrom, the thermosensor 20 having a bimetallic bottom portion 21 closely spaced from the bottom 13 of the metal tube 12. The thermosensor 20 is further provided with a head 22 extending above the electrode head 17 and threadedly secured thereto. Extending from the thermosensor head 22 is an electrical lead 23 suitably connected to a meter 25 for converting voltage measurements generated by the bimetallic bottom portion 21 of the thermosensor 20 into temperature readings.

An electrode terminal 30 is electrically connected to the metal tube 12 and extends radially outwardly from the tube 12 to the annular periphery of the electrode head 17, thereby to provide an electrical connection from the reference half cell formed by the metal tube 12 and the electrolyte 15. Finally, there is provided an ion diffusion barrier 35 in the form of a ceramic plug having capillary openings which provide ionic communication between the electrolyte 15 inside the reference electrode 10 and an electrolyte in communication with the plug 35 and another half-cell.

Referring now to FIG. 3 of the drawings, there is disclosed a schematic illustration of an electrochemical cell 40 using the reference electrode 10 of the present invention. The electrochemical cell 40 includes a housing 41 containing at least two working electrodes 42 and 43. An electrolyte 45 is in communication with both working electrodes 42, 43 and in communication with the reference electrode 10, the electrolyte level being designated by the reference numeral 46. To measure the voltage between the reference electrode 10 and either one of the working electrodes 42, 43, there is provided a volt meter 50 having a terminal 51 connected by a conductor 52 to the electrode terminal 30 of the reference electrode 10. The other terminal 61 of the volt meter 50 is connected via a conductor 62 to one terminal of a switch 63, the other terminal of the switch 63 being connected by a conductor 64 to a terminal 65 on the working electrode 42. The terminal 61 of the volt meter 50 is also connected via conductor 62 to one terminal of a switch 66 the other terminal of which is connected by a conductor 67 to a terminal 68 on the working electrode 43. The electrical circuit thus described permits voltage measurements to be obtained between the reference electrode 10 and either of the working electrodes 42, 43 by the simple expedient of closing one of the switches 63,66 while opening the other. This voltage in combination with the meter 25 which measures the temperature of the reference electrode 10 provides the required data.

In a constructional example of the reference electrode 10 of the present invention, an aluminum oxide tubing about 18 to 20 inches long having an 0.125 inch outside diameter and an 0.062 inch inside diameter was used as the tubular housing 11. Nickel tubing having an outside diameter of 0.04 inches and inside diameter of 0.02 inches was used for the electrode half-cell. A chromel-alumel thermocouple in a stainless steel sheathe having an outside diameter of 0.01 inches was used as the thermosensor 20. The electrolyte 15 was the lithium-chloride potassium chloride eutectic which is 58.2 mol percent lithium chloride having a melting point of 352° C.; the electrolyte also was saturated with lithium sulfide and had lithium sulfide powder passing through a 270 mesh screen distributed throughout to maintain constant the sulfide ion activity in the electrolyte 15. The ion diffusion barrier 35 was an aluminum oxide plug which provides the required capillary communication between the electrolyte 15 inside the reference electrode 10 and the cell electrolyte 45 when the reference electrode 10 is in a cell 40 with the working electrodes 42,43.

The reference electrode 10 of the present invention has been used in an electrochemical cell 40 to determine the potential of various working electrodes 42,43. After the reference electrode 10 was fabricated, the nickel tube 12 is annodized by a repeated small 10 micro amp pulses until 2-3 coulombs per square centimeter of nickel sulfide had been deposited on the outer surface 16 of the nickel tube 12. When the nickel sulfide has been deposited on the outer surface 16 of the nickel tube 12, there exists an electrical double-layer between the adjacent electrolyte 15 and the metal tube 12. Specifically, the electrical double-layer between the metal tube 12 and the adjacent electrolyte 15 results in temperature dependent electrode potential at the surface 16 of the metal tube 12. This electrode potential is fixed at a specific temperature at constant sulfide ion activity so that by knowing the temperature of the electrode 11, the electrode potential can be calculated by obtaining voltage measurements between the reference electrode 10 and a standard well known in the art such as the Al/Li-Al($\alpha+\beta$)/Li+ half cell. After the relationship between temperature and electrode potential has been established for a particular reference electrode 10 against a previously known standard, the reference electrode 10 may be used in a cell 40 to help design working electrodes 42,43 by establishing the potentials or electron pressure for the electrodes 42,43 at specific temperatures and operating conditions.

Providing voltage measurements between the reference electrode 10 and a working electrode 42,43 at a specified temperature permits determination of the electrode potential at the surface of the working electrode, and it is this value which assists in electrode design and it is for this reason, among others, that the reference electrode 10 is useful. In order for the electrode potential to remain constant at a given temperature, it is also required that the sulfide ion activity remain constant. In the reference electrode 10 of the present invention, the lithium chloride-potassium chloride eutectic is saturated with lithium sulfide, and solid lithium sulfide particles are provided to ensure that the solution remains saturated with lithium sulfide during use of the reference electrode.

The nickel tube 12 and the ceramic housing 11 have a low mass on the order of fifty to sixty grams so the time constant for the electrode to come to thermal and electrochemical equilibrium for a change in temperature is small. This permits close correlation between the temperature at the outer surface 16 of the metal tube 12 and the changes in voltage between the reference electrode 10 and the working electrodes 42,43. The small mass and quick response time of reference electrode 10 is a distinct advantage when compared to available calibration standards.

Although the described reference electrode 10 utilized a nickel sulfide/sulfide half-cell with a stainless steel sheathed thermocouple and is applicable and has been used in high temperature lithium-aluminum/metal sulfide battery systems, other combinations are useful such as a silver plated or sheathed thermistor with a silver sulfate half-cell for use in a lead acid battery system. The preferred reference electrode 10 used an aluminum oxide ion diffusion barrier but other ceramics such as yettrium oxide are acceptable. The lithium-chloride-potassium chloride eutectic is the preferred electrolyte, but other electrolytes are well known to those skilled in the art.

The reference electrode 10, as before stated, is particularly useful in determining the electrode potential at the surface of the working electrodes 42,43. To that end, voltage measurements must be obtained to permit determination of the electrode potential. Simultaneously, accurate temperature measurements must also be obtained.

In the system schematically illustrated in FIG. 3, an electrochemical cell 40 is provided with an electrolyte 45 such as the lithium chloride-potassium chloride eutectic but without lithium sulfide. The working electrodes 42,43 may be a lithium-aluminum electrode or an iron sulfide electrode, by way of illustration. When the switch 63 is closed and the switch 66 open, voltage meter 50 will provide the voltage or potential difference between the reference electrode 10 and the working electrode 42. Simultaneously the temperature of the electrochemical double-layer at the surface 16 of the reference electrode 10 is provided by the meter 25 connected to the thermosensor 20 in the reference electrode. FIG. 3 and the circuit therein illustrated is merely schematic, but illustrates the nature of the invention.

While there has been described herein what is considered to be the preferred embodiment of the present invention, various modifications or alterations may be made therein by one skilled in the art without departing from the true scope of the invention which is defined in the claims attached hereto.

The embodiments of the invention in which an exclusive property or privelege is claimed are defined as follows:

1. A multifunctional reference electrode, comprising a metal tube closed at one end, a means inside said metal tube near said closed end for measuring the temperature thereof, a housing surrounding said metal tube, an electrode terminal electrically connected to said metal tube extending outside of said housing, an electrolyte between said housing and the outer surface of said metal tube, and an ion diffusion barrier plug associated with said housing in contact with said electrolyte, whereby said multifunctional reference electrode provides a temperature dependent electrode potential at the surface of said metal tube where an electrochemical double layer exists between the metal tube outer surface and said electrolyte in combination with means for measuring the temperature of said metal tube.

2. The multifunctional sensor set forth in claim 1, wherein said means for measuring the temperature of said metal tube includes a sensing portion positioned near the bottom of said metal tube.

3. The multifunctional sensor set forth in claim 1, wherein said ion diffusion barrier is porous ceramic at the bottom of said housing.

4. The multifunctional sensor set forth in claim 1, wherein said metal tube is nickel and said electrolyte is an eutectic of lithium chloride and potassium chloride saturated with sulfide ions.

5. The multifunctional sensor set forth in claim 4, and further including solid lithium sulfide particles distributed in said electrolyte to maintain the sulfide ion concentration at a saturated level in said electrolyte.

6. The multifunctional sensor set forth in claim 1, wherein said metal tube is silver and said electrolyte is an eutectic of lithium chloride and potassium chloride saturated with sulfide ions.

7. The multifunctional sensor set forth in claim 6, and further comprising solid lithium sulfide particles distributed in said electrolyte to maintain the sulfide ion concentration at a saturated level in said electrolyte.

8. A combination electrochemical cell and reference electrode comprising a plurality of working electrodes and a reference electrode and a first electrolyte in communication with said working and said reference electrodes, said reference electrode including a metal tube closed at one end said metal tube acting as internal contact for said reference electrode, means inside said metal tube electrically insulated therefrom for measuring the temperature thereof near said closed end, a housing surrounding said metal tube, a second electrolyte having a fixed anion activity between said housing and the outer surface of said metal tube providing a temperature dependent electrode potential at the surface of said metal tube when an electrochemical double layer exists between the metal tube outer surface and said second electrolyte, an ion diffusion barrier associated with said housing providing communication between ions of said first and second electrolytes, and means for measuring the temperature of said reference electrode and a working electrode adjacent thereto and the potential difference between said reference electrode and said working electrodes, whereby the fixed anion activity and measured temperature of said reference electrode and the potential difference between said reference electrode and said working electrodes provides a value for the electrode potential at the working electrodes.

9. The combination set forth in claim 8, wherein said metal tube is nickel and said second electrolyte contains an alkali metal sulfide.

10. The combination set forth in claim 9, wherein said second electrolyte is an eutectic of lithium chloride and potassium chloride having solid lithium sulfide present therein.

11. The combination set forth in claim 8, wherein said metal tube is a silver and said second electrolyte contains an alkali metal sulfide.

12. The combination set forth in claim 11, wherein said second electrolyte is an eutectic of lithium chloride and potassium chloride having solid lithium sulfide particles distributed therein to maintain the sulfide ion at a saturated level.

13. The combination set forth in claim 8, wherein said reference electrode has a low mass with said metal tube and said housing weighing in the range of from about 50 to about 60 grams.

14. The combination set forth in claim 8, wherein said means for measuring the temperature of said metal tube is a thermocouple with the bimetallic portion thereof being positioned near the bottom of said metal tube.

15. The combination set forth in claim 14, wherein said ion diffusion barrier is a porous ceramic plug at the bottom of said housing.

* * * * *